US011883452B2

(12) United States Patent
Sun et al.

(10) Patent No.: US 11,883,452 B2
(45) Date of Patent: Jan. 30, 2024

(54) USE OF COMBINATION OR COMPOSITION OF RADIX ET RHIZOMA NOTOGINSENG AND ASPIRIN

(71) Applicant: CHINESE ACADEMY OF MEDICINAL SCIENCES INSTITUTE OF MEDICINAL PLANT DEVELOPMENT, Beijing (CN)

(72) Inventors: Xiaobo Sun, Beijing (CN); Xiangbao Meng, Beijing (CN); Guibo Sun, Beijing (CN); Huibo Xu, Beijing (CN)

(73) Assignee: CHINESE ACADEMY OF MEDICAL SCIENCES INSTITUTE OF MEDICINAL PLANT DEVELOPMENT, Beijing (CN)

( * ) Notice: Subject to any disclaimer, the term of this patent is extended or adjusted under 35 U.S.C. 154(b) by 143 days.

(21) Appl. No.: 16/650,638

(22) PCT Filed: Dec. 13, 2017

(86) PCT No.: PCT/CN2017/115813
§ 371 (c)(1),
(2) Date: Jun. 16, 2020

(87) PCT Pub. No.: WO2019/056592
PCT Pub. Date: Mar. 28, 2019

(65) Prior Publication Data
US 2020/0330538 A1 Oct. 22, 2020

(30) Foreign Application Priority Data
Sep. 25, 2017 (CN) .......................... 201710873249.7

(51) Int. Cl.
*A61K 36/258* (2006.01)
*A61K 31/616* (2006.01)

(52) U.S. Cl.
CPC .......... *A61K 36/258* (2013.01); *A61K 31/616* (2013.01)

(58) Field of Classification Search
None
See application file for complete search history.

(56) References Cited

U.S. PATENT DOCUMENTS

2011/0160153 A1* 6/2011 Lan ...................... A61K 36/258
514/26

FOREIGN PATENT DOCUMENTS

| CN | 1872110 | A | 12/2006 |
| CN | 101708204 | A | 5/2010 |
| CN | 101708204 | * | 4/2012 |
| CN | 105582017 | A | 5/2016 |

OTHER PUBLICATIONS

The Chinese Journal of Clinical Pharmacology "Press Release of Phased Research Achievements of "Ari Therapy" for Benefiting Cardiovascular and Cerebrovascular Disease Patients". 2017.*
DrugBank (Panax Notoginseng Root).*
Tian et al. "Effect of Panax Notoginseng Saponins on the Pharmacokinetics of Aspirin in Rats" 2017.*
Mayo Clinic Congenital Heart Diseases in Adults.*
PCT International Search Report and Written Opinion of the International Searching Authority for PCT/CN2017/115813, dated Jun. 14, 2018, 22 pages.
Chinese Office Action cited in Chinese Application No. 201710873249.7 dated Jun. 3, 2020, 18 pages.
"Press Release of Phased Research Achievements of "Ari Therapy" for benefiting Cardiovascular and Cerebrovascular Disease Patients (Press release), The Chinese Journal of Clinical Pharmacology." The Chinese Journal of Clinical Pharmacology, vol. 33, No. 8, Apr. 30, 2017, pp. 768.
Gao, Jianling et al. "An effective Study on Intervening Recurrence of Cerebral Infarction with Aspirin Plus Notoginseng Pharmaceutics." Clinical Journal of Chinese Medicine, vol. 7, No. 1, Jan. 10, 2015, pp. 72-73.
Teng, Dan et al. "Clinical research progress of notoginseng saponins combined with aspirin in the treatment of cardiovascular and cerebrovascular diseases." Journal of Modern Health, Mar. 2016, pp. 65.
Yang, Qing-Feng et al. "Influence of Panax Notoginseng Saponins Combined with Aspirin on Senile Coronary Heart Disease by Thromboela-stogram." J Nanjing Univ Tradit Chin Med, vol. 32, No. 5, Sep. 2016, pp. 425-427.
Source: China Pharmaceutical News. "Antithrombotic Chemical Drugs Combined With Traditional Chinese Medicine Can Increase Efficacy and Reduce "Side Effects"". Mar. 29, 2017 10:52.
He et al. "Radix/Rhizoma Notoginseng extract (Sanchitongtshu) for ischemic stroke: A randomized controlled study". Phytomedicine 18 (2011) 437-442, published electronically Oct. 8, 2010.
Office Action of corresponding Japanese Patent Application No. 2020537819 dated Sep. 28, 2021.
U.S. Department of Health and Human Services Food and Drug Administration Center for Drug Evaluation and Research (CDER), "Guidance for Industry: Estimating the Maximum Safe Starting Dose in Initial Clinical Trials for Therapeutics in Adult Healthy Volunteers," Pharmacology and Toxicology, http://www.fda.gov/cder/guidance/index.htm, Jul. 2005, 30 pages.

(Continued)

*Primary Examiner* — Danah Al-Awadi
(74) *Attorney, Agent, or Firm* — Dinsmore & Shohl LLP

(57) ABSTRACT

An application of a combination or composition of *Radix et Rhizoma Notoginseng* and aspirin in the preparation of a drug for preventing and treating cardiovascular and cerebrovascular diseases, the combination or composition being as follows: the dose range of *Radix et Rhizoma Notoginseng* is 25-500 mg/d, and the dose range of aspirin is 20-700 mg/d. The *Radix et Rhizoma Notoginseng* comprises commercially available products, *Radix et Rhizoma Notoginseng*, an extract prepared from *Radix et Rhizoma Notoginseng*, an active ingredient of *Radix et Rhizoma Notoginseng* and a preparation of *Radix et Rhizoma Notoginseng*, and so on. *Radix et Rhizoma Notoginseng* and aspirin have a synergistic effect, while reducing gastric mucosal damage caused by aspirin.

11 Claims, 2 Drawing Sheets

(56) References Cited

OTHER PUBLICATIONS

Lansberg et al., "Antithrombotic and Thrombolytic Therapy for Ischemic Stroke," CHEST 2012; 141(2)(Suppl), e601S-e636S, 36 pages.
Kernan et al., "Guidelines for the Prevention of Stroke in Patients With Stroke and Transient Ischemic Attack a Guideline for Healthcare Professionals From the American Heart Association/American Stroke Association," Stroke, 2014; 45:2160-2236, 77 pages.
Decision of Refusal for JP Application No. JP2020-537819, dated Jun. 7, 2022, 3 pages.
Combination of antithrombotic chemicals and Traditional Chinese Medicine can increase the effect and reduce the "side effects".

\* cited by examiner

USE OF COMBINATION OR COMPOSITION OF RADIX ET RHIZOMA NOTOGINSENG AND ASPIRIN

CROSS-REFERENCE TO RELATED APPLICATIONS

The present application is a National Phase Entry of International Application No. PCT/CN2017-115813, entitled "NOVEL USE OF COMBINATION OR COMPOSITION OF *PANAX NOTOGINSENG* AND ASPIRIN" and filed on Dec. 13, 2017, which claims priority to Chinese Patent Application No. 201710873249.7 filed with the National Intellectual Property Administration, PRC on Sep. 25, 2017, the entire contents of both are incorporated herein by reference.

TECHNICAL FIELD

The invention belongs to the field of traditional Chinese medicine, and specifically relates to use of combination or composition of *Radix* et *Rhizoma Notoginseng* and a chemical drug aspirin for the prevention or treatment of cardiovascular and cerebrovascular diseases, in particular relates to the combination of *Radix* et *Rhizoma Notoginseng* including medicine products made from various medicinal materials such as roots, rhizomes, rootlets, and stem leaves, an extract prepared from *Radix* et *Rhizoma Notoginseng*, an active ingredient of *Radix* et *Rhizoma Notoginseng* and a preparation of *Radix* et *Rhizoma Notoginseng* with aspirin for use in prevention or treatment of cardiovascular and cerebrovascular diseases, reducing gastric mucosal damage in rats caused by aspirin and reducing the risk of bleeding, showing the effect of synergism and toxicity reduction.

BACKGROUND OF THE INVENTION

A secondary prevention of cardiovascular and cerebrovascular diseases refers to the early detection, early diagnosis and early treatment of patients who have developed coronary heart disease, cerebral infarction and other atherosclerotic vascular diseases, the purpose of which is to improve symptoms, reduce the mortality rate and disability rate, prevent disease progresses, improve the prognosis, and prevent the recurrences of coronary heart disease, cerebral infarction and the like. At present, aspirin is a commonly used drug in clinic for secondary prevention of cardiovascular and cerebrovascular diseases, mainly having the effects of preventing platelet aggregation and release, improving the balance of prostaglandins and thromboxane A2, preventing arteriosclerosis thrombosis, and preventing the recurrence of coronary heart disease or cerebral infarction. However, aspirin may cause some adverse reactions such as gastrointestinal bleeding, intracranial hemorrhage, and aspirin resistance, which affects its use.

Chinese medicine has multi-channel and multi-target effects, and has unique advantages in the control of cardiovascular and cerebrovascular diseases. Chinese medicine has been widely recognized by clinicians because it attaches great importance to overall regulation and has little toxic and side effects.

*Radix* et *Rhizoma Notoginseng* is the root of *Panax notoginseng* (Burk.) F. H. Chen which is a perennial herb of the family Araliaceae. *Radix* et *Rhizoma Notoginseng* is sweet and slightly bitter in taste, damp in property, and distributes to liver and stomach channels. Crude *Radix* et *Rhizoma Notoginseng* has effects of eliminating blood stasis, arresting bleeding, relieving swelling and alleviating pain, and are used to treat hemoptysis, hematemesis, traumatic bleeding, and traumatic swelling and pain; Cooked *Radix* et *Rhizoma Notoginseng* has effects of nourishing blood and promoting blood circulation, and are used to treat blood loss and anemia. Therefore, *Radix* et *Rhizoma Notoginseng* is an important member in the Traditional Chinese Medicine for the treatment of different types of bleeding and bruises in vivo and vitro. Total saponins from *Radix* et *Rhizoma Notoginseng* are an effective active ingredients in *Radix* et *Rhizoma Notoginseng*. Studies in China and abroad have proved that the total saponins from *Radix* et *Rhizoma Notoginseng* have anti-oxidative stress and anti-inflammatory effects, and have definite neuroprotective effects in vivo and vitro, and can be used to improve cerebral ischemia, inhibit platelet aggregation, reduce blood viscosity, and prevent blood clots, etc. However, there has been no in-depth research on the mechanism of action of total saponins from *Radix* et *Rhizoma Notoginseng* for cardiovascular and cerebrovascular diseases, and no report about the combination use of total saponins from *Radix* et *Rhizoma Notoginseng* with antiplatelet drugs such as aspirin. In the present invention it is found that the combination use of the total saponins from *Radix* et *Rhizoma Notoginseng* and aspirin shows a synergistic effect in improving efficacy and reducing toxicity, thereby improving its activity and providing a safer and more effective composition and method for clinical treatment and prevention of cardiovascular and cerebrovascular diseases.

SUMMARY OF THE INVENTION

The invention provides a use of combination or composition of *Radix* et *Rhizoma Notoginseng* and aspirin in a method for prevention or treatment of cardiovascular and cerebrovascular diseases, preferably in a primary or secondary prevention of cardiovascular and cerebrovascular diseases.

The invention provides a use of combination or composition of *Radix* et *Rhizoma Notoginseng* and aspirin in a method for prevention or treatment of cardiovascular and cerebrovascular diseases and for reducing gastric mucosal damage in rats caused by aspirin at the same time.

In the present invention, a combination or composition of *Radix* et *Rhizoma Notoginseng* and aspirin is used for the prevention and treatment of cardiovascular and cerebrovascular diseases, showing a synergistic effect and a good effect on the prevention and treatment of cardiovascular and cerebrovascular diseases and at the same time reducing gastric mucosal damage caused by aspirin.

*Radix* et *Rhizoma Notoginseng* in the present invention is selected from the group consisting of commercially available products, *Radix* et *Rhizoma Notoginseng* including products made from various medicinal materials such as roots, rhizomes, rootlets and stem leaves, an extract prepared from *Radix* et *Rhizoma Notoginseng* according to a conventional method, an active ingredient of *Radix* et *Rhizoma Notoginseng* and preparations of *Radix* et *Rhizoma Notoginseng* including injections, oral preparations and other preparations.

The extract prepared from *Radix* et *Rhizoma Notoginseng* in the present invention can be prepared by the following methods: water extraction method, water extraction and alcohol precipitation method, extraction method, dipping method, percolation method, reflux extraction method, continuous reflux extraction method, and macroporous resin adsorption method, etc. In order to improve its efficacy, it is preferable to extract *Radix* et *Rhizoma Notoginseng* according to but not limit to the following method: collecting and pulverizing roots of *Panax notoginseng* (Burk.) F. H. Chen, extracting the roots with ethanol, recovering ethanol from the resulted extraction solution, concentrating the extraction solution, loading the concentrated extraction solution to a macroporous adsorption resin column, eluting with water and ethanol, and collecting the ethanol eluent, recovering ethanol from the eluent, and drying the eluent.

The extract prepared from *Radix* et *Rhizoma Notoginseng* comprises total saponins in an amount of 55-90% by weight.

Preferably, the present invention provides a use of combination or composition of total saponins from *Radix* et *Rhizoma Notoginseng* and aspirin in a method for prevention or treatment of cardiovascular and cerebrovascular diseases, and at the same time reducing gastric mucosal damage caused by aspirin.

The invention provides a pharmaceutical composition, comprising *Radix* et *Rhizoma Notoginseng*, aspirin and a pharmaceutically acceptable carrier, prepared into any clinically acceptable dosage form. Preferably, the combination refers to a combination of total saponins from *Radix* et *Rhizoma Notoginseng* and aspirin.

Preferably, in a combination of the total saponins from *Radix* et *Rhizoma Notoginseng* and aspirin, the total saponins from *Radix* et *Rhizoma Notoginseng* have a dose range of 25-500 mg/d and aspirin has a dose range of 20-700 mg/d. More preferably, the total saponins from *Radix* et *Rhizoma Notoginseng* have a dose range of 250-500 mg/d and aspirin has a dose range of 81-100 mg/d.

Preferably, in a composition of the total saponins from *Radix* et *Rhizoma Notoginseng* and aspirin, the total saponins from *Radix* et *Rhizoma Notoginseng* and aspirin has a weight ratio of (3-94):(6-97), preferably (71-86):(14-29).

In the present invention, the combination or composition is preferably administered for a period of 1 week to long-term.

The dosage form of the pharmaceutical composition of the present invention is selected from the group consisting of tablets including orally disintegrating tablets, sustained-release tablets, orally disintegrating tablets, sustained-release tablets and controlled-release tablets; capsules including sustained-release capsules and controlled-release capsules; oral solution, syrups, granules, pills, water injections, lyophilized powder injections, sterile powder injections and infusions.

The pharmaceutically acceptable carrier is selected from the group consisting of fillers, adhesives, lubricants, disintegrants, co-solvents, surfactants, adsorption carriers, solvents, antioxidants, co-solvents, adsorbents, osmotic pressure adjusting agents and pH adjusting agents.

In the present invention, the use of combination or composition of *Radix* et *Rhizoma Notoginseng* and aspirin in a method for prevention or treatment of cardiovascular and cerebrovascular diseases shows a synergistic effect in improving efficacy and reducing toxicity, and has good effects on the prevention and treatment of cardiovascular and cerebrovascular diseases and at the same time reducing gastric mucosal damage in rats caused by aspirin.

DETAILED DESCRIPTION OF THE EMBODIMENTS

Figure 1:
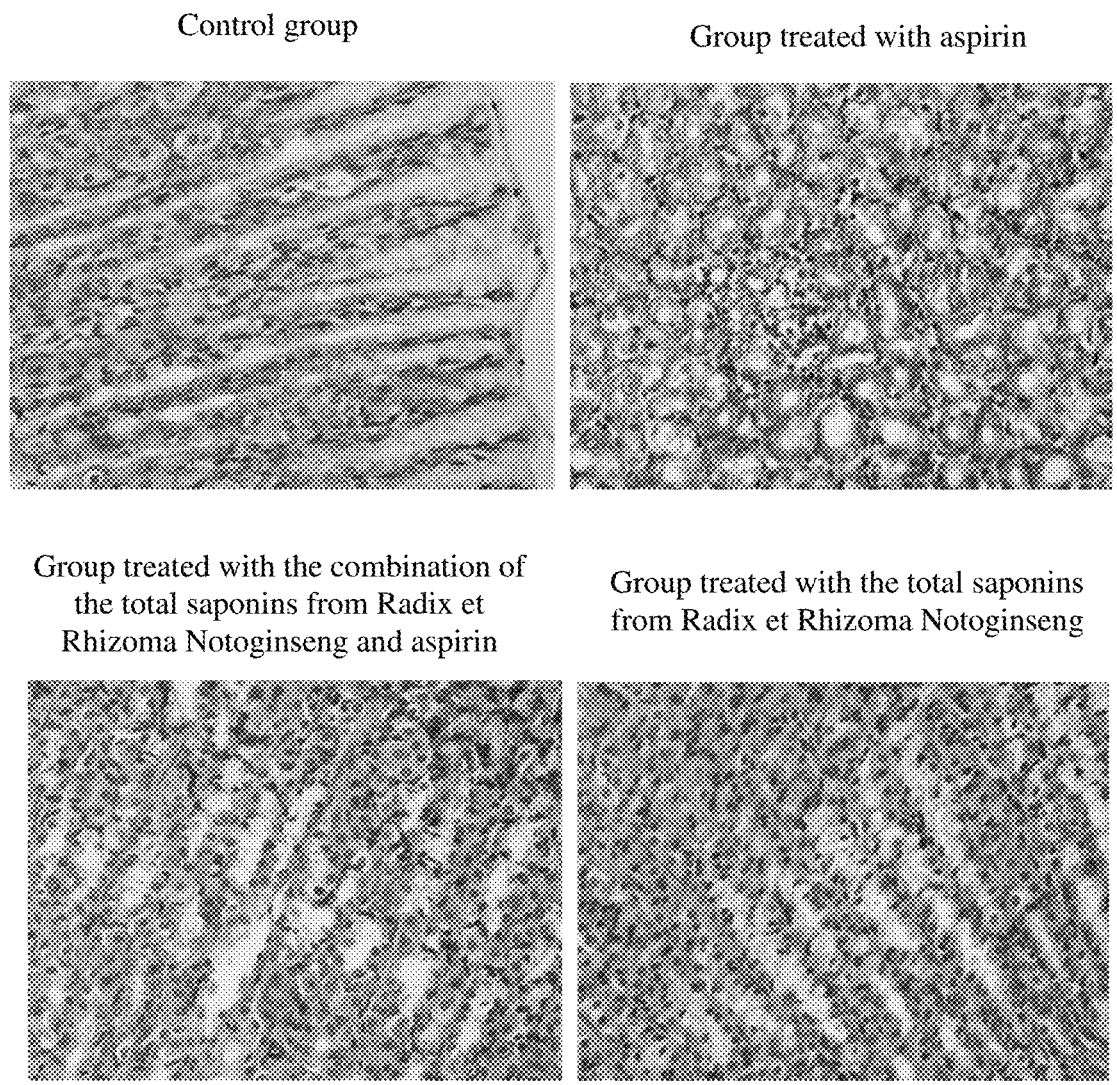
FIG. 1 shows that total saponins from *Radix* et *Rhizoma Notoginseng* can significantly reduce gastric mucosal damage in rats caused by aspirin.

The beneficial effects of the combination or composition described in the present invention will be further described below through experimental examples. These experimental examples include the prevention and treatment effect of the composition of the present invention on cerebrovascular diseases.

Example 1: Synergistic Effect of the Combination of the Total Saponins from *Radix Et Rhizoma Notoginseng* and Aspirin on Myocardial Ischemia Reperfusion Injury in Rats 1. Experimental Animal Healthy male SD rats weighted 280-300 g were provided by Beijing Vital River Laboratory Animal Company and raised in the Animal Center of the Institute of Medicinal Plant Development, Chinese Academy of Medical Sciences. The animals were tested after one week of adaptive feeding. The experiment was approved by the Experimental Animal Management and Animal Welfare Committee of the Chinese Academy of Medical Sciences/Beijing Union Medical College and the Institute of Medicinal Plant Development before the experiment.

2. Experimental Method 2.1 Animal Grouping and Administration Methods 240 male SD rats were randomly divided into 8 groups, with 30 rats in each group, including a sham operated group, a myocardial ischemia reperfusion injury model group, a group treated with the total saponins from *Radix* et *Rhizoma Notoginseng* at a dosage of 50 mg/kg, a group treated with aspirin at a dosage of 10 mg/kg, a group treated with aspirin at a dosage 5 mg/kg, a group treated with the combination of the total saponins from *Radix* et *Rhizoma Notoginseng* at a dosage of 50 mg/kg and aspirin at a dosage of 5 mg/kg. Rats in the groups treated with the total saponins from *Radix* et *Rhizoma Notoginseng* and/or aspirin were administrated intragastrically with the total saponins from *Radix* et *Rhizoma Notoginseng* and/or aspirin for a week, and rats in the sham operated group and model group were administrated intragastrically with an equivalent volume of distilled water.

2.2 Model Establishing

The rats were anesthetized by intraperitoneal injection of pentobarbital sodium at a dose of 40 mg/kg body weight, and were connected to a small animal ventilator through an oral cannula, with a respiratory rate of 70 breaths/min, a respiratory ratio of 1:1, and a tidal volume of 1 mL. Real time electrocardiograms of the rats were recorded on a multi-lead physiological recorder available from AD Instruments. Thoracotomy was performed on the rats. An incision of 2 to 3 cm was made at a place between the 3rd and 4th ribs and about 0.5 cm from the left side of the sternum, a chest expander was used to open the ribs, and the pericardium was cut when exhaling to expose the heart. Myocardial ischemia was established by ligating the left coronary artery. A needle with a piece of 6-0 silk thread was inserted to pass through the myocardial surface about 1 to 1.5 mm, with a span of 2 to 3 mm, between the pulmonary artery cone and the left atrial appendage, about 2 mm below the left atrial appendage. After being stabilized for 5 minutes, the silk thread was passed through a disposable intravenous infusion hose with a length of about 3.5 cm. After the silk thread was pulled out, the silk thread was gently lifted, and the hose was pushed down and was fixed with a hemostatic forceps. After 30 minutes of ischemia, the hemostatic forceps was released, and the thread was removed to perform reperfusion for 1 d, 3 d, 7 d, and 14 d to establish a myocardial ischemia-reperfusion injury model. The ligation was considered successful if: the ST segment was elevated, and the color of local myocardial tissue changed from red to gray; and after 30 minutes of reperfusion, the ST segment fell by more than 50%, and the color of myocardial tissue changed from gray to red.

2.3 Measurement of Volume of Myocardial Infarction

Myocardial infarction volumes were evaluated by triphenyl tetrazolium chloride (TTC) staining. Rats (n=5) were sacrificed after 24 hours of reperfusion. Hearts were quickly removed, placed in a refrigerator to short freeze at −20° C., then placed onto an ice tray and cut into 5 slices with a thickness of 2 mm. The slices were placed in 1.5 mL 2% TTC solution for incubation in the dark for 30 min, and then fixed in 10% paraformaldehyde overnight, and then photographed for analysis. Myocardial infarction volumes were evaluated and calculated using Image-Pro plus 5.1 software 2.4 Detection of Indexes of Three Myocardial Enzymes After the reperfusion was completed, blood was taken from the abdominal aorta and analyzed on an automatic biochemical analyzer to detect the levels of three myocardial enzymes (AST, LDH, CK) in plasma.

3. Experimental Results 3.1 Combination of the Total Saponins from *Radix Et Rhizoma Notoginseng* and Aspirin is Capable of Reducing the Volume of Myocardial Infarction Induced by Myocardial Ischemia-Reperfusion Injury As shown in Table 1, compared with the sham operated group, rats in the myocardial ischemia-reperfusion injury model group exhibit significant increase in the volume of myocardial infarction; Compared with the model group, rats in the groups treated with the total saponins from *Radix et Rhizoma Notoginseng* and/or aspirin exhibit significant decrease in the volume of myocardial infarction. Compared with the group treated with aspirin of 10 mg/kg alone, rats in the group treated with the combination of the total saponins from *Radix et Rhizoma Notoginseng* of 50 mg/kg and aspirin of 5 mg/kg exhibit significant decrease in the volume of myocardial infarction.

TABLE 1

Combination of the total saponins from Radix et Rhizoma Notoginseng and aspirin is capable of reducing the volume of myocardial infarction induced by myocardial ischemia-reperfusion injury (n = 10, $\bar{x} \pm s$)

| Groups | Dose | Myocardial infarction volume (%) |
|---|---|---|
| Sham operated group | | 0.00 ± 0.00 |
| Model group | — | 14.35 ± 1.64## |
| Group treated with total saponins from Radix et Rhizoma Notoginseng | 50 mg/kg | 9.34 ± 0.83** |
| Group treated with aspirin | 10 mg/kg | 8.75 ± 0.51** |
| Group treated with aspirin | 5 mg/kg | 9.88 ± 0.64** |
| Group treated with total saponins from Radix et Rhizoma Notoginseng and aspirin | 50 mg/kg + 5 mg/kg | 6.55 ± 0.37** && |

Note:
Compared with the sham operated group, P## < 0.01; Compared with model group, P** < 0.01; Compared with group treated with the total saponins from Radix et Rhizoma Notoginseng or aspirin alone, P && < 0.01.

3.2 Combination of the Total Saponins from *Radix Et Rhizoma Notoginseng* and Aspirin is Capable of Reducing AST, LDH and CK Activities of Myocardial Tissues in Myocardial Ischemia-Reperfusion Injury Rats As shown in Table 2, compared with the sham operated group, AST, LDH, and CK activities of myocardial tissues increased significantly in myocardial ischemia-reperfusion injury model group; Compared with the model group, AST, LDH, and CK activities of myocardial tissues reduced significantly in the group treated with the total saponins from *Radix et Rhizoma Notoginseng* and aspirin. Compared with the group treated with aspirin of 10 mg/kg alone, AST, LDH, and CK activities of myocardial tissues reduced significantly in the group treated with the combination of the total saponins from *Radix et Rhizoma Notoginseng* of 50 mg/kg and aspirin of 5 mg/kg.

TABLE 2

Combination of the total saponins from Radix et Rhizoma Notoginseng and aspirin is capable of reducing AST, LDH and CK activities of myocardial tissues in myocardial ischemia - reperfusion injury rats (n = 10, $\bar{x} \pm s$)

| Groups | Dose | AST(U/L) | LDH(U/L) | CK(U/L) |
|---|---|---|---|---|
| Sham operated group | — | 102.21 ± 11.36 | 440.38 ± 21.96 | 673.58 ± 41.88 |
| Model group | — | 628.36 ± 38.48## | 2234.74 ± 150.45## | 4136.85 ± 212.48## |
| Group treated with the total saponins from Radix et Rhizoma Notoginseng | 50 mg/kg | 214.39 ± 18.33** | 843.91 ± 41.31** | 1432.22 ± 152.47** |
| Group treated with aspirin | 10 mg/kg | 204.32 ± 17.25** | 811.85 ± 35.25** | 1222.54 ± 131.63** |
| Group treated with aspirin | 5 mg/kg | 312.48 ± 21.85** | 1105.54 ± 104.44** | 1823.49 ± 124.31** |

TABLE 2-continued

Combination of the total saponins from Radix et Rhizoma Notoginseng and aspirin is capable of reducing AST, LDH and CK activities of myocardial tissues in myocardial ischemia - reperfusion injury rats (n = 10, $\bar{x} \pm s$)

| Groups | Dose | AST(U/L) | LDH(U/L) | CK(U/L) |
|---|---|---|---|---|
| Group treated with the total saponins from Radix et Rhizoma Notoginseng and aspirin | 50 mg/kg + 5 mg/kg | 173.12 ± 13.42** && | 663.12 ± 38.86** && | 1112.28 ± 108.27** && |

Note:
Compared with the sham operated group, P## < 0.01; Compared with model group, P** < 0.01; Compared with group treated with the total saponins from Radix et Rhizoma Notoginseng or aspirin alone, P && < 0.01.

Example 2: Synergistic Effect of the Combination of the Total Saponins from *Radix Et Rhizoma Notoginseng* and Aspirin on Cerebral Ischemia-Reperfusion Injury in Rats 1. Experimental Animal Healthy male SD rats were provided by Beijing Vital River Laboratory Animal Company and raised in the Animal Center of the Institute of Medicinal Plant Development, Chinese Academy of Medical Sciences. The animals were tested after one week of adaptive feeding. The experiment was approved by the Experimental Animal Management and Animal Welfare Committee of the Chinese Academy of Medical Sciences/Beijing Union Medical College and the Institute of Medicinal Plant Development before the experiment.

2. Experimental Method 2.1 Animal Grouping and Administration Methods 240 male SD rats were randomly divided into 8 groups, with 30 rats in each group, including a sham operated group, a middle cerebral artery occlusion (MCAO/R) model group, a group treated with the total saponins from *Radix et Rhizoma Notoginseng* at a dosage of 50 mg/kg, a group treated with aspirin at a dosage of 10 mg/kg, a group treated with aspirin at a dosage of 5 mg/kg, a group treated with the combination of the total saponins from *Radix et Rhizoma Notoginseng* at a dosage of 50 mg/kg and aspirin at a dosage of 5 mg/kg. The rats in the groups treated with the total saponins from *Radix et Rhizoma Notoginseng* and/or aspirin were administrated intragastrically with the total saponins from *Radix et Rhizoma Notoginseng* and/or aspirin for a week before MCAO, and the rats in the sham operated group and model group were administrated intragastrically with an equivalent volume of distilled water.

2.2 Middle Cerebral Artery Occlusion (MCAO/R) Model Establishing

Middle cerebral artery occlusion (MCAO) model was established by thread embolization method. The surgical procedure was carried out under strictly aseptic conditions mainly according to the following steps: The rats were anesthetized by intraperitoneal injection of ketamine (80 mg/kg) and xylazine (10 mg/kg). The common carotid artery (CCA), external carotid artery (ECA) and internal carotid artery (ICA) were fully exposed, the common carotid artery was clamped with a vascular clip, and the branches of the external carotid artery were electrocoagulated with a bipolar electrocoagulation forceps. The main trunk of the external carotid artery was freed and ligated at 3 to 4 mm from the bifurcation of the common carotid artery. The internal carotid artery was temporarily clamped with a vascular clip. Corneal scissors were used to make a small incision in the external carotid artery. A 4-0 monofilament nylon thread coated with methylpolysiloxane was inserted and was tied a loose knot at the small incision of the external carotid artery to block the blood reflux of the internal carotid artery. The clip was removed from the internal carotid artery, and the nylon thread was gently pushed into the internal carotid artery to reach the intracranial anterior cerebral artery to block an incision of the middle cerebral artery (MCA), with an insertion depth of about 18-22 mm. The clip was removed from the common carotid artery, and the subcutaneous tissue and skin were sutured layer by layer after disinfection, and 2 hours later the nylon thread was slowly withdrawn to perform reperfusion for 24 hours. The operation to the sham operated group is the same as the above except that nylon thread is not inserted. The rectum of all rats was maintained at a temperature of 37° C. throughout the experiment.

2.3 Neurological Evaluation

Neurobehavior of all rats were evaluated according to Longa's five-grade scoring standard. The Longa score system was as follows: grade 0, normal function, showing no neurological deficit; grade 1, weakened function, showing failure to extension of left forelimb; grade 2, severely weakened function, showing left circling and left forelimb paralysis, and the rats twisting toward the damaged area when tails of the rats were lifted; grade 3, showing dumping to the left while walking; grade 4, showing limb paralysis and conscious coma; and grade 5, showing death.

2.4 Measurement of Brain Water Content

Water contents of brain tissues were determined by Wet-Dry Weight Method. Firstly, brain tissues of the rats (n=10) were placed in a crucible, and weighed to obtain a wet weight respectively. Then, the numbered brain tissues were placed in an oven to bake at 110° C. for more than 24 h to a constant weight, and weighed to obtain a dry weight. The percentage of water content of brain tissues was calculated according to the following formula: water content of brain tissue=(wet weight-dry weight)/wet weight×100%.

2.5 Measurement of Volume of Cerebral Infarction

Cerebral infarction volumes were determined by triphenyl tetrazolium chloride (TTC) staining. Rats (n=5) were sacrificed after 24 hours of reperfusion. The whole brain was quickly removed, placed in a refrigerator short freeze at −20° C., then placed onto an ice tray to remove the olfactory bulb. The forebrain was cut along the coronal plane into 5 slices with a thickness of 2 mm. Brain slices were placed in 1.5 mL 2% TTC solution for incubation in the dark for 30 min, and then fixed in 10% paraformaldehyde overnight, and then photographed for analysis. Cerebral infarction volumes were evaluated and calculated using Image-Pro plus 5.1 software.

2.5 Determination of Maximum Platelet Aggregation Rate 3.6 mL of blood was taken from the rats (n=10), anticoagulated with 3.8% sodium citrate (9:1), centrifuged at 150 g for 10 min to separate a platelet-rich plasma, and then centrifuged at 1500 g for 10 min to obtain a supernatant, which was platelet-poor plasma. 0.3 mL of platelet-rich plasma was placed in a turbidimetric tube, the transmittance was adjusted with the platelet-poor plasma, and adenosine diphosphate (ADP) was used as an inducing agent (final concentration is 2 μmol/L). Maximum aggregation within 5 minutes and maximum aggregation time of platelets in platelet-rich plasma were detected with a blood agglutination instrument.

2.6 Detection of Oxidative Stress Indicators, Canine Urea and Inflammatory Factors 5 mL of blood was taken from the abdominal aorta of the rats (n=8), and centrifuged at 3000 rpm for 10 min to obtain a serum. Hippocampus and cerebral cortex were separated from the brain tissue, homogenized, and centrifuged at 3000 rpm for 10 min to obtain a supernatant. Serum MDA, SOD, CAT and GSH-Px levels were detected with kits available from Nanjing Jiancheng; levels of canine urea and inflammatory response indicators MCP-1, TNF-α, IL-1β, IL-4, IL-6 and IL-10 were detected with ELISA kits.

2.7 Statistics

SPSS statistical software was used for statistical analysis. Unpaired t test and One-way ANOVA were used for statistical analysis of measurement data. P<0.05 indicated statistical difference.

3. Experimental Results 3.1 Combination of the Total Saponins from *Radix* Et *Rhizoma Notoginseng* and Aspirin is Capable of Improving Neurological Deficits Induced by MCAO/R in Rats As shown in Table 3, compared with the sham operated group, the neurological deficit score increased significantly in the MCAO/R model group; Compared with the MCAO/R model group, the neurological deficit score reduced significantly in the groups treated with the total saponins from *Radix* et *Rhizoma Notoginseng* and/or aspirin. Compared with the group treated with aspirin of 10 mg/kg alone, the neurological deficit score reduced significantly in the group treated with the combination of the total saponins from *Radix* et *Rhizoma Notoginseng* of 50 mg/kg and aspirin of 5 mg/kg.

TABLE 3

Combination of the total saponins from Radix et Rhizoma Notoginseng and aspirin is capable of improving neurological deficits induced by MCAO/R in rats (n = 10, $\bar{x} \pm s$)

| Groups | Dose | Score |
|---|---|---|
| Sham operated group | | 0.00 ± 0.00 |
| MCAO/R model group | — | 3.33 ± 0.50 ## |
| Group treated with the total saponins from Radix et Rhizoma Notoginseng | 50 mg/kg | 1.14 ± 0.38 ** |
| Group treated with aspirin | 10 mg/kg | 1.08 ± 0.36 ** |
| Group treated with aspirin | 5 mg/kg | 1.83 ± 0.75 ** |

TABLE 3-continued

Combination of the total saponins from Radix et Rhizoma Notoginseng and aspirin is capable of improving neurological deficits induced by MCAO/R in rats (n = 10, $\bar{x} \pm s$)

| Groups | Dose | Score |
|---|---|---|
| Group treated with the combination of the total saponins from Radix et Rhizoma Notoginseng and aspirin | 50 mg/kg + 5 mg/kg | 1.00 ± 0.00 ** & |

Note:
Compared with the sham operated group, P# < 0.05, P## < 0.01; Compared with MCAO/R model group, P* < 0.05, P** < 0.01; Compared with group treated with the total saponins from Radix et Rhizoma Notoginseng or aspirin alone, P & < 0.05.

3.2 Combination of the Total Saponins from *Radix* Et *Rhizoma Notoginseng* and Aspirin is Capable of Reducing Cerebral Infarction Volumes Induced by MCAO/R in Rats As shown in Table 4, compared with the sham operated group, the volume of cerebral infarction increased significantly in the MCAO/R model group; compared with the MCAO/R model group, the volume of cerebral infarction reduced significantly in the groups treated with the total saponins from *Radix* et *Rhizoma Notoginseng* and/or aspirin. Compared with the group treated with aspirin of 10 mg/kg alone, the volume of cerebral infarction reduced significantly in the group treated with the combination of the total saponins from *Radix* et *Rhizoma Notoginseng* of 50 mg/kg and aspirin of 5 mg/kg.

TABLE 4

Combination of the total saponins from Radix et Rhizoma Notoginseng and aspirin is capable of reducing cerebral infarction volumes induced by MCAO/R in rats (n = 10, $\bar{x} \pm s$)

| Groups | Dose | Volume of cerebral infarction |
|---|---|---|
| Sham operated group | | 0.00 ± 0.00 |
| MCAO/R model group | — | 24.47 ± 5.16## |
| Group treated with the total saponins from Radix et Rhizoma Notoginseng | 50 mg/kg | 14.03 ± 1.94** |
| Group treated with aspirin | 10 mg/kg | 13.96 ± 1.28** |
| Group treated with aspirin | 5 mg/kg | 16.08 ± 3.05** |
| Group treated with the combination of the total saponins from Radix et Rhizoma Notoginseng and aspirin | 50 mg/kg + 5 mg/kg | 6.15 ± 1.20** && |

Note:
Compared with the sham operated group, P# < 0.05, P## < 0.01; Compared with MCAO/R model group, P** < 0.01; Compared with group treated with the total saponins from Radix et Rhizoma Notoginseng or aspirin alone, P && < 0.01.

3.3 Combination of the Total Saponins from *Radix* Et *Rhizoma Notoginseng* and Aspirin is Capable of Reducing the Maximum Platelet Aggregation Rate As shown in Table 5, compared with the sham operated group, the maximum platelet aggregation rate increased significantly in the MCAO/R model group; compared with the MCAO/R model group, the maximum platelet aggregation rate reduced significantly in the groups treated with the total saponins from *Radix* et *Rhizoma Notoginseng* and/or aspirin. Compared with the group treated with aspirin of 10 mg/kg alone, the maximum platelet aggregation rate in the group treated with the combination of the total saponins from Radix et Rhizoma Notoginseng of 50 mg/kg and aspirin of 5 mg/kg increased, but the difference is not statistically significant.

TABLE 5

Combination of the total saponins from Radix et Rhizoma Notoginseng and aspirin is capable of reducing the maximum platelet aggregation rate (n = 10, $\bar{x} \pm s$)

| Groups | Dose | Maximum platelet aggregation rate (%) |
|---|---|---|
| Sham operated group | — | 61.61 ± 8.37 |
| MCAO/R model group | — | 97.79 ± 9.65## |
| Group treated with the total saponins from Radix et Rhizoma Notoginseng | 50 mg/kg | 67.85 ± 25.43** |
| Group treated with aspirin | 10 mg/kg | 62.63 ± 18.55** |
| Group treated with aspirin | 5 mg/kg | 56.80 ± 17.82** |
| Group treated with the combination of the total saponins from Radix et Rhizoma Notoginseng and aspirin | 50 mg/kg + 5 mg/kg | 64.75 ± 13.11** |

Note:
Compared with the sham operated group, P# < 0.05, P## < 0.01; Compared with MCAO/R model group, P* < 0.05, P** < 0.01.

3.4 Combination of the Total Saponins from *Radix Et Rhizoma Notoginseng* and Aspirin is Capable of Reducing Inflammatory Factors and Increasing Anti-Inflammatory Factors in the Serum As shown in Table 6, compared with the sham operated group, serum IL-1β, IL-4, IL-6, IL-10, TNF-α and MCP-1 increased significantly in the MCAO/R model group; Compared with the MCAO/R model group, serum IL-1β, IL-6, TNF-α, and MCP-1 decreased significantly, while IL-4 and IL-10 increased significantly in the groups treated with the total saponins from *Radix* et *Rhizoma Notoginseng* and/or aspirin. Compared with the group treated with aspirin of 10 mg/kg alone, serum IL-6 and MCP-1 decreased significantly and IL-10 increased significantly in the group treated with the combination of the total saponins from *Radix* et *Rhizoma Notoginseng* of 50 mg/kg and aspirin of 5 mg/kg.

TABLE 6

Combination of the total saponins from Radix et Rhizoma Notoginseng and aspirin is capable of reducing inflammatory factors and increasing anti-inflammatory factors in the serum (n = 10, $\bar{x} \pm s$)

| Groups | Dose | IL-1β (pg/mL) | IL-4 (pg/mL) | IL-6 (pg/mL) |
|---|---|---|---|---|
| Sham operated group | — | 86.68 ± 16.77 | 12.02 ± 2.25 | 36.04 ± 2.61 |
| MCAO/R model group | — | 293.07 ± 33.36## | 24.72 ± 3.43## | 55.61 ± 2.39## |
| Group treated with the total saponins from Radix et Rhizoma Notoginseng | 50 mg/kg | 207.06 ± 21.20** | 30.06 ± 2.43** | 50.57 ± 2.70** |
| Group treated with aspirin | 10 mg/kg | 189.69 ± 14.63** | 35.45 ± 2.23** | 47.15 ± 3.88** |
| Group treated with aspirin | 5 mg/kg | 168.58 ± 18.04** | 36.57 ± 4.54** | 47.12 ± 3.59** |
| Group treated with the total saponins from Radix et Rhizoma Notoginseng and aspirin | 50 mg/kg + 5 mg/kg | 172.32 ± 17.30** | 40.98 ± 3.34** | 41.39 ± 3.18**& |

| Groups | IL-10 (pg/mL) | MCP-1 (pg/mL) | TNF-α (pg/mL) |
|---|---|---|---|
| Sham operated group | 18.26 ± 2.50 | 27.28 ± 4.71 | 50.00 ± 3.32 |
| MCAO/R model group | 35.27 ± 2.81## | 134.82 ± 9.97## | 60.27 ± 2.68## |
| Group treated with total saponins from Radix et Rhizoma Notoginseng | 50.24 ± 4.33** | 110.91 ± 11.34** | 55.32 ± 4.45* |
| Group treated with aspirin | 51.11 + 5.55** | 100.74 ± 8.55** | 54.85 ± 3.33** |
| Group treated with aspirin | 41.15 ± 4.30** | 100.69 ± 6.13** | 56.08 ± 1.61** |
| Group treated with the total saponins from Radix et Rhizoma Notoginseng and aspirin | 52.74 ± 6.13**&& | 85.93 ± 4.55**&& | 53.59 ± 5.17** |

Note:
Compared with the sham operated group, P# < 0.05, P## < 0.01; Compared with MCAO/R model group, P* < 0.05, P** < 0.01; Compared with group treated with the total saponins from Radix et Rhizoma Notoginseng or aspirin alone, P& < 0.05, P&& < 0.01.

3.5 Combination of the Total Saponins from *Radix Et Rhizoma Notoginseng* and Aspirin is Capable of Reducing Canine Urea Levels in Serum, Hippocampus and Cerebral Cortex Tissue As shown in Table 7, compared with the sham operated group, canine urea levels in serum, hippocampus and cerebral cortex tissue increased significantly in the MCAO/R model group; Compared with the MCAO/R model group, canine urea levels in serum, hippocampus and cerebral cortex tissue reduced significantly in the groups treated with the total saponins from *Radix* et *Rhizoma Notoginseng* and/or aspirin. Compared with the group treated with aspirin of 10 mg/kg alone, canine urea levels in serum, hippocampus and cerebral cortex tissue significantly decreased in the group treated with the combination of the total saponins from *Radix* et *Rhizoma Notoginseng* of 50 mg/kg and aspirin of 5 mg/kg.

TABLE 7

Combination of total saponins from Radix et Rhizoma Notoginseng and aspirin can reduce canine urea levels in serum, hippocampus and cerebral cortex tissue (n = 10, $\bar{x} \pm s$)

| Groups | Dose | Canine urea levels in serum (μg/L) | Canine urea levels in hippocampus (μg/L) | Canine urea levels in cerebral cortex tissue (μg/L) |
|---|---|---|---|---|
| Sham operated group | — | 11.56 ± 0.97 | 1.33 ± 0.19 | 6.93 ± 0.25 |
| MCAO/R model group | — | 23.53 ± 1.93## | 2.47 ± 0.27## | 10.01 ± 0.28## |
| Group treated with total saponins from Radix et Rhizoma Notoginseng | 50 mg/kg | 20.90 ± 1.35* | 2.16 ± 0.23* | 9.53 ± 0.47* |
| Group treated with aspirin | 10 mg/kg | 17.25 ± 144** | 2.01 ± 0.12** | 8.12 ± 0.66** |
| Group treated with aspirin | 5 mg/kg | 18.00 ± 1.34** | 2.11 ± 0.10** | 8.95 ± 0.44** |
| Group treated with total saponins from Radix et Rhizoma Notoginseng and aspirin | 50 mg/kg + 5 mg/kg | 16.53 ± 1.00**& | 1.94 ± 0.17**& | 7.97 ± 0.38**&& |

Note:
Compared with the sham operated group, P# < 0.05, P## < 0.01; Compared with MCAO/R model group, P* < 0.05, P** < 0.01; Compared with group treated with the total saponins from Radix et Rhizoma Notoginseng or aspirin alone, P& < 0.05, P&& < 0.01.

Example 3: Total Saponins from *Radix* Et *Rhizoma Notoginseng* can Inhibit Gastric Mucosal Damage Caused by Aspirin 1. Experimental Animal Healthy male SD rats weighted 280-300 g were provided by Beijing Vital River Laboratory Animal Company and raised in the Animal Center of the Institute of Medicinal Plant Development, Chinese Academy of Medical Sciences. The animals were tested after one week of adaptive feeding. The experiment was approved by the Experimental Animal Management and Animal Welfare Committee of the Chinese Academy of Medical Sciences/Beijing Union Medical College and the Institute of Medicinal Plant Development before the experiment.

2. Experimental Method 2.1 Animal Grouping and Administration Methods 40 male SD rats were randomly divided into 4 groups, with 10 rats in each group, including a control group, a group treated with aspirin at a dosage of 10 mg/kg, a group treated with the total saponins from *Radix* et *Rhizoma Notoginseng* at a dosage of 100 mg/kg and aspirin at a dosage of 10 mg/kg, and a group treated with the total saponins from *Radix* et *Rhizoma Notoginseng* at a dosage of 100 mg/kg. The rats in the groups treated with the total saponins from *Radix* et *Rhizoma Notoginseng* and aspirin were administrated intragastrically with the total saponins from *Radix* et *Rhizoma Notoginseng* and aspirin daily for 4 weeks, and the rats in the control group were administrated intragastrically with an equivalent volume of normal saline daily.

2.2 HE Staining to Detect Pathological Changes of Gastric Mucosa

After 4 weeks of administration, gastric tissues were taken from rats in each group and fixed with 4% formaldehyde solution, routinely embedded in paraffin and cut into slices, and stained with HE to observe the degree of inflammatory lesions in the tissues.

2.3 Detection of Ultrastructure of Duodenal Villi with Transmission Electron Microscope After 4 weeks of administration, the duodenum was collected from rats in each group of rats and fixed in 2.5% glutaraldehyde buffer for 2 h, then washed with PH 7.4 buffer three times, and then soaked with 1% osmium tetroxide for 30 min, dehydrated with graded alcohol and acetone, and then embedded in epoxy resin 812. Ultra-thin slices were prepared, copper grids of 200 grid units were taken, the ultra-thin slices were again impregnated with uranyl acetate and lead citrate, and then analyzed under the electron microscope to observe changes in the ultrastructure of the duodenum in rats of each group.

3. Experimental Results 3.1 the Total Saponins from *Radix* Et *Rhizoma Notoginseng* is Capable of Significantly Reducing Gastric Mucosal Damage Caused by Aspirin in Rats As shown in FIG. 1, compared with the control group, gastric mucosal epithelial cells were necrotic and inflammatory cells infiltrated in the group treated with aspirin. Compared with the group treated with aspirin, the total saponins from *Radix* et *Rhizoma Notoginseng* can significantly reduce gastric mucosal epithelial cell necrosis and inflammatory cell infiltration caused by aspirin. The total saponins from *Radix* et *Rhizoma Notoginseng* alone had no significant effect on rat gastric mucosa.

Figure 2:
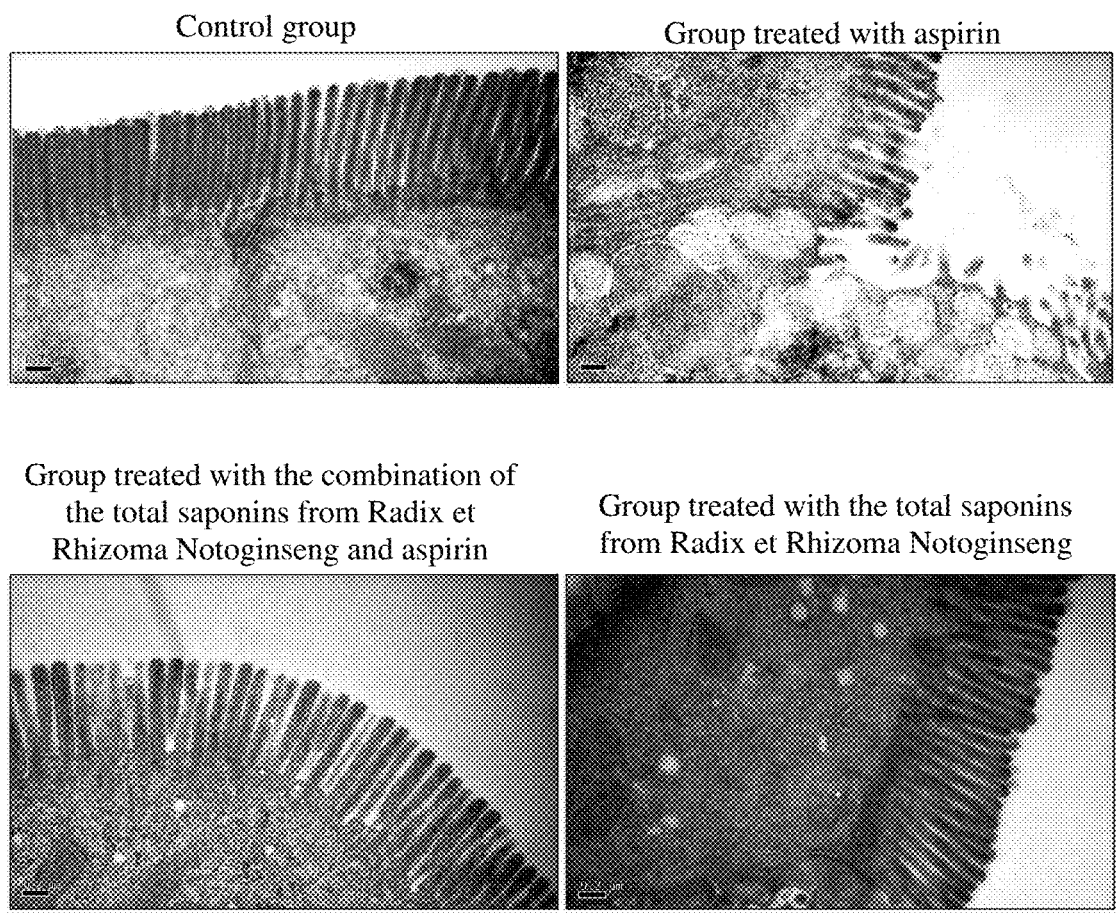
FIG. 2 shows that total saponins from *Radix* et *Rhizoma Notoginseng* can significantly reduce duodenal microvilli damage in rats caused by aspirin.

3.2 the Total Saponins from *Radix* Et *Rhizoma Notoginseng* can Significantly Reduce Duodenal Microvilli Damage Caused by Aspirin As shown in FIG. 2, compared with the control group, the microvilli on the duodenal surface decreased in the group treated with aspirin. Compared with the group treated with aspirin, the total saponins from *Radix* et *Rhizoma Notoginseng* can significantly reduce the reduction of microvilli on the duodenal surface caused by aspirin. The total saponins from *Radix* et *Rhizoma Notoginseng* alone had no significant effect on rat gastric mucosa.

Obviously, the above examples of the present invention are only examples for clearly illustrating the present invention, rather than limiting the embodiments of the present invention. For those skilled in the art, other different forms of changes or alterations can be made based on the above description. There is no need to exhaustively list all implementations. However, these obvious changes or alterations derived from the spirit of the present invention are still within the protection scope of the present invention.

The invention claimed is:

1. A method for treatment of cardiovascular and cerebrovascular diseases, comprising administering a combination of total saponins from *Radix* et *Rhizoma Notoginseng* and aspirin to a subject in need,
    wherein the total saponins from *Radix* et *Rhizoma Notoginseng* has a dose of 50 mg/kg and aspirin has a dose of 5 mg/kg; and
    wherein the cardiovascular disease is selected from the group consisting of coronary heart disease, acute myocardial infarction and atherosclerotic vascular diseases; and
    wherein the cerebrovascular disease is selected from the group consisting of ischemic brain stroke and thrombotic cerebrovascular disease.

2. The method according to claim 1, wherein the combination of total saponins from *Radix* et *Rhizoma Notoginseng* and aspirin also reduce gastric mucosal damage in rats caused by aspirin.

3. The method according to claim 1, wherein the combination of total saponins from *Radix* et *Rhizoma Notoginseng* and aspirin are administered for a period of 1 week or greater than 1 week.

4. The method according to claim 1, wherein the total saponins from *Radix* et *Rhizoma Notoginseng* is mixed with aspirin and a pharmaceutically acceptable carrier to prepare into any clinically acceptable dosage form.

5. The method according to claim 4, wherein the dosage form is selected from the group consisting of tablets, capsules, oral solution, syrups, granules, pills, water injections, lyophilized powder injections, sterile powder injections and infusions.

6. The method according to claim 5, wherein the pharmaceutically acceptable carrier is selected from the group consisting of fillers, adhesives, lubricants, disintegrants, co-solvents, surfactants, adsorption carriers, solvents, antioxidants, adsorbents, osmotic pressure adjusting agents and pH adjusting agents.

7. The method according to claim 5, wherein the tablets are selected from orally disintegrating tablets, sustained-release tablets, or controlled-release tablets.

8. The method according to claim 5, wherein the capsules are selected from sustained-release capsules or controlled-release capsules.

9. The method according to claim 1, wherein administering the combination of total saponins from *Radix* et *Rhizoma Notoginseng* and aspirin inhibits gastrointestinal mucosal damage caused by aspirin.

10. The method according to claim 9, wherein the gastrointestinal mucosal damage is gastric mucosa damage.

11. The method according to claim 9, wherein the gastrointestinal mucosal damage is duodenal microvilli damage.

* * * * *